United States Patent [19]

Hasegawa et al.

[11] Patent Number: 4,794,105

[45] Date of Patent: Dec. 27, 1988

[54] METHOD FOR TREATMENT OF SWINE DYSENTERY

[75] Inventors: Toru Hasegawa; Setsuo Harada; Toshiyuki Yamazaki, all of Kawanishi, Japan

[73] Assignee: Takeda Chemical Industries, Ltd., Osaka, Japan

[21] Appl. No.: 878,363

[22] Filed: Jun. 24, 1986

[30] Foreign Application Priority Data

Jun. 27, 1985 [JP] Japan .............................. 60-142329

[51] Int. Cl.[4] .............................................. A61K 31/70

[52] U.S. Cl. ...................................................... 514/25

[58] Field of Search .......................... 536/16.8; 514/25

[56] References Cited

U.S. PATENT DOCUMENTS 3,100,176 8/1963 Ehrlich et al. ........................ 167/65

4,425,356 1/1984 Narukawa et al. ................ 424/279

FOREIGN PATENT DOCUMENTS 10933 6/1967 Japan .

OTHER PUBLICATIONS

The Merck Index, 9th Ed., 1976, p. 646.

Pittenger et al., Antibiotics and Chemotherapy (Washington, D.C.), vol. 3, No. 12, pp. 1268–1278, (1953).

Wakisaka et al., The Journal of Antibiotics, vol. 33, No. 7, pp. 695–704, (1980).

*Primary Examiner*—Frederick E. Waddell

*Attorney, Agent, or Firm*—Wenderoth, Lind & Ponack

[57] ABSTRACT

Hygromycin, epihygromycin and a mixture thereof have potent inhibitory activity against *Treponema hyodysenteriae* and are useful for treatment of swine dysentery.

4 Claims, No Drawings

METHOD FOR TREATMENT OF SWINE DYSENTERY

TECHNOLOGICAL FIELD

The present invention relates to a method for treatment of swine dysentery, which comprises administering to swine, as an active ingredient, an effective amount of hygromycin, epihygromycin or a mixture thereof.

BACKGROUND ART

Many chemotherapeutic agents and antibiotics have been evaluated for prevention and treatment of swine dysentery, and certain synthetic antimicrobial agents in the quinoxaline, nitroimidazole and nitrofuran series and antibiotics in the macrolide and diterpene series have been put to use. Prophylactic methods using vaccines have also been investigated but none have been developed to the practically useful stage as yet. Thus, chemotherapeutics and antibiotics are playing leading roles in the prophylaxis and treatment of swine dysentery today.

Swine dysentery is an infectious disease in pigs which is principally caused by *Treponema hyodysenteriae*, large spirochaete, and its chief manifestations are mucohemorrhagic diarrheal stools. This epidemic in swine herds is slow to spread as compared with other acute infections but as a huge number of organisms are contained in their feces, the surroundings are quickly contaminated and it is acknowledged to be extremely difficult to clean the swine quarters where this epidemic has once taken hold.

The long-term losses to the feeder pig producer due to the growth retardation and decreased feed conversion induced by swine dysentery are uncalculably great. While the aforementioned drugs have been used just for the purpose of avoiding such losses, their effects are not necessarily satisfactory.

Regarding hygromycin, R. C. Pittenberg et al. discovered it in a culture of *Streptomyces hygroscopicus* in 1953 and reported for the first time its antimicrobial spectrum and the results of their infection study [Antibiotics Annual, 1953–1954, P. 157]. Then, in 1957, R. L. Mann et al. determined its chemical structure [Journal of The American Chemical Society, 79, 120 (1957)]. It was also shown that *Streptomyces atrofaciens* produces the same substance (U.S. Pat. No. 3,100,176; Aug. 6, 1963). On the other hand, Sumiki et al. reported on the antituberculous antibiotic homomycin produced by *Streptomyces noboritoensis* as an analog of hygromycin [Journal of Antibiotics, Series A, 8, 170 (1955)]. However, the subsequent comparative study of this antibiotic and hygromycin by K. Isono et al. showed that the two antibiotics are actually the same substances [Journal of Antibiotics 10, 21 (1957)]. More recently, ST-4331 reported by K. Kakinuma et al. was identified with hygromycin and its absolute structure was presented [Journal of Antibiotics, 29, 771, (1976)]. However, Wakisaka et al. corrected the suggested absolute structure of hygromycin and presented the existence of epihygromycin and its absolute structure [Journal of Antibiotics 33, 695 (1980)].

As regards the biological activity of hygromycin, this antibiotic is known to have strong inhibitory activity against gram-positive and gram-negative bacteria and acid-fast bacteria, especially human type tubercle bacilli, and has also been shown, by animal experiments, to produce therapeutic effects in infections caused by bacteria, inclusive of tubercle bacilli, Borrelia and certain viruses. However, it has not been suggested that hygromycin is effective against swine dysentery.

DISCLOSURE OF THE INVENTION

The present invention provides a method for treatment of swine dysentery, which comprises administering to swine, as an active ingredient, an effective amount of hygromycin, epihygromycin or a mixture thereof.

Hygromycin can be produced not only by the methods described in the above-mentioned literature but also by the method described in Japanese Patent Examined Publication No. 33-1248 (1958) employing *Streptomyces noboritoensis* [Institute for Fermentation, Osaka, IFO 13065; List of Cultures, 7th Edition (1984)].

Hygromycin, epihygromycin and a mixture thereof are highly safe, and these substances can be orally administered alone or in an admixture thereof to swine for treatment of swine dysentery. Swine may also be administered orally or parenterally with these compounds in combination with other carriers.

When hygromycin and epihygromycin are used in an admixture thereof, their proportions are optional but the preferred ratio is about 0.3 to 1 weight part of epihygromycin to 1 weight part of hygromycin and the more preferred ratio is 0.3 to 0.5 weight part of epihygromycin to 1 weight part of hygromycin.

In animal production, it is common practice to rear animals in herds and, if swine dysentery is discovered in a herd, to cull out and treat the affected individuals or administer medicated food ration to all the animals in the herd without isolating the dysenteric animals. Such practices of medication with or without culling, using hygromycin, epihygromycin or a mixture thereof are also encompassed by the present invention.

The therapeutic agent for swine dysentery according to the present invention can be prepared as follows:

Hygromycin, epihygromycin or a mixture thereof is optionally diluted with a solid or liquid diluent or stabilized by coating (for prevention of its destruction due to contact with a base) according to a conventional procedure, for instance, and prepared into such dosage forms as powders, fine powders, granules, tablets, liquids, pastes, capsules, injections or the like, or added to a food ration or drinking water directly or after dispersion in a diluent. The diluent may be any material that is physiologically harmless, and preferably is one that can be a food ration or a constituent of a food ration. Examples of said solid diluent include barley meal, wheat meal, rye meal, corn meal, soybean meal, soybean cake, rape cake, rice husks, rice bran, defatted rice bran, sweet potato meal, potato meal, soybean curd cake, starch, lactose, sucrose, glucose, fructose, yeast, spent yeast, fishmeal, talc, acid clay, clay and so on. Examples of said liquid diluent include water, physiological saline, and an organic solvent which is physiologically harmless such as ethanol or propylene glycol. Other appropriate auxiliary agents such as emulsifiers, dispersants, suspending agents, wetting agents, concentrating agents or thickeners, gelling agents, solubilizers, etc. may also be added in suitable amounts. Further, preservatives, fungicides, antimicrobial agents (carbadox, demetridazole, etc.), antibiotics (e.g. tiamulin, lincomycin, etc.), enzyme preparations and lactobacillus preparations may be added, and optionally the resulting compositions may be further supplemented with vitamins, minerals, amino acids and other substances.

The dosage of the therapeutic agent for swine dysentery according to the present invention can be selected in consideration of the pig's age, condition, route of administration, etc. When the agent is to be administered to a swine herd where an outbreak of dysentery has been confirmed, for instance, the preferred dose is about 0.05 to 25 mg/kg/day as hygromycin, epihygromycin or a mixture thereof, the much preferred dose being about 0.4 to 4 mg/kg/day. In such applications, it is preferred to add hygromycin, epihygromycin or a mixture thereof to the ration for swine at a level of about 1 to 500 ppm, preferably about 2 to 200 ppm, most preferably about 15 to 150 ppm, and to give the ratio to the swine. For the treatment of affected individuals, the preferred dose level is about 0.1 to 50 mg/kg/day (the much preferred dose level: about 0.4 to 4 mg/kg/day) as hygromycin, epihygromycin or a mixture thereof and in such applications, it is preferable to add the active agent to the ration at a level of about 2 to 500 ppm, particularly about 2.5 to 200 ppm, more particularly about 15 to 150 ppm, and to give the diseased pig the medicated ration. As regards an injection, the preferred dosage is 0.25 to 25 mg/kg/day (the much preferred dosage: about 2.5 to 25 mg/kg/day) and the active agent is preferably formulated by the routine pharmacological procedure to provide an injectable composition of about 1 to 1000 mg/ml, preferably about 1 to 500 mg/ml, far more preferably about 40 to 400 mg/ml. The injectable composition may be a suspension, solution or emulsion of the active agent in a physiologically acceptable oily (e.g. soy bean oil, sesame oil) or aqueous (e.g. physiological saline, aqueous glucose solution, aqueous propylene glycol solution) medium, and may then include such auxiliary agents as a suspending agent, stabilizer and/or dispersing agent, and, if necessary, preservatives such as benzyl alcohol as well as buffer agents. The composition, or the active compound, may be a reconstitutable powder and in such a case, the powder is reconstituted with a suitable vehicle, such as sterile distilled water for injection, on administration.

The following examples are intended to illustrate the present invention in further detail and the present invention should not be limited thereto.

EXAMPLE 1

The therapeutic agent for swine dysentery according to the present invention or a premix thereof can be manufactured by adding hygromycin, epihygromycin or a mixture thereof to the basal ration of Table 1 or a partial composition thereof at a suitable concentration.

TABLE 1

| | Composition of Basal Ration (%) | |
|---|---|---|
| Materials | Milk replacer B | Feed for assay of performance of meat production |
| Corn | 20.0 | 22.0 |
| Milo | | 22.0 |
| Barley meal | 19.0 | 22.0 |
| Wheat meal | 14.0 | |
| Soybean meal | 4.0 | |
| Wheat bran | 6.8 | 12.0 |
| Defatted rice bran | 4.0 | 4.0 |
| Fish meal | 3.0 | 4.0 |
| Soybean cake | | 4.0 |
| Skim milk powder | 9.78 | |
| Defatted soybean | 5.0 | |
| Dried whey | 5.0 | |

TABLE 1-continued

| | Composition of Basal Ration (%) | |
|---|---|---|
| Materials | Milk replacer B | Feed for assay of performance of meat production |
| Alfalfa meal | | 2.5 |
| Glucose | 5.0 | |
| Yeast for feed | 2.0 | |
| Powdered fat | 1.5 | |
| Calcium carbonate | | 1.5 |
| Sodium chloride | | 0.5 |
| Tricalcium phosphate | 0.7 | 0.8 |
| Saccharin | 0.02 | |
| Vitamin-mineral mixture | 0.2[a] | 0.4[b] |
| DL-methionine | | 0.1 |
| Total | 100.0 | 100.0 |

[a]In one kilogram, 2,500,000 I.U. of vitamin A, 500,000 I.U. of vitamin $D_3$, 0.75 g of vitamin E, 1 g of vitamin $B_1$ nitrate, 1.5 g of vitamin $B_2$, 0.25 g of vitamin $B_6$, 1 mg of vitamin $B_{12}$, 3.5 g of calcium pantothenate, 7.5 g of nicotinamide, 50 g of choline hydrochloride, 50 g of iron, 5 g of copper, 25 g of zinc, 15 g of manganese, 0.25 g of cobalt and 0.1 g of iodine.
[b]A composition consisting of A Mixture, B Mixture, and C Mixture in a ratio of 0.15:0.15:0.1.
A Mixture: 5% of manganese, 5% of iron, 1% of copper, 6% of zinc and 0.1% of iodine
B Mixture: In one gram, 10,000 I.U. of vitamin A and 2000 I.U. of vitamin $D_3$
C Mixture: In one kilogram, 1 g of vitamin $B_1$ nitrate, 7 g of vitamin $B_2$, 0.5 g of vitamin $B_6$, 6 g of nicotinamide, 10.9 g of calcium pantothenate, and 57.6 g of choline Further, 10 μg of vitamin $B_{12}$ is added.

EXAMPLE 2 INJECTION

A 25 ml vial is aseptically filled with 4 g of a powder of hygromycin, epihygromycin or a mixture thereof as prepared by a sterile procedure and 180 mg of sodium chloride, followed by sealing to produce an injection. In using the injection, 20 ml of sterile distilled water is injected into the vial to prepare a solution containing 200 mg/ml of the above active component.

EXPERIMENTS (i) The antimicrobial activity values of hygromycin, epihygromycin and the known anti-swine dysentery agent, lincomycin, against *Treponema hyodysenteriae* are shown in Table 2.

TABLE 2

| | Minimum inhibitory concentration (MIC: μg/ml)[2-4] | | | |
|---|---|---|---|---|
| Drug | CD1[1] | DJ70P1[1] | MK2[1] | 78/A[1] |
| Hygromycin | 6.25 | 6.25 | 6.25 | 6.25 |
| Epihygromycin | 12.5 | 12.5 | 12.5 | 12.5 |
| Mixture[5] | 6.25 | 6.25 | 6.25 | 6.25 |
| Lincomycin | 25 | 25 | 25 | 25 |

[1]Strains: Strains of *Treponema hyodysenteriae* isolated from the mucohemorrhagic diarrheal feces of dysenteric pigs in Japan.
[2]Method of antimicrobial assay: agar plate dilution.
[3]Inoculum size: a loopful (ca. 0.5 μl) of $10^6$ CFU/ml.
[4]Culture conditions: anaerobic culture at 37° C. for 2 days in Gaspak jar (BBL).
[5]Mixture: Crystals containing hygromycin (68%), epihygromycin (24%) and moisture (8%).

(ii) An experimental study on the antidysenteric effects of hygromycin and epihygromycin was conducted in experimental infection with *Treponema hyodysenteriae* in mice.

Using Ta: CF#1 mice and, as the infective strain, *Treponema hyodysenteriae* DJ70P3, the experiment was carried out in the mouse infection model with *Treponema hyodysenteriae* described in Zentralblatt für Bakteriologie, Mikrobiologie und Hygiene A257, 348–356 (1984). The test agent was dissolved in sterile water and administered by gastric gavage or subcutaneous injection twice, i.e. day 1 and 2 after infection. Seven days after infection, the caecal lesion was observed and recorded. The cecum taken together with its contents was homogenized and the number of *Treponema hyodysenteriae* were bacterioglogically counted. As shown in Tables 3 and 4, excellent protective effects against the infection were found in the drug-treated groups.

TABLE 3

| Test group | Dosage (mg/kg/ day × 2) | Number of mice with caecal lesion/number of mice tested | Number of mice from which the organisms were recovered/number of mice tested |
|---|---|---|---|
| Infected, untreated control | — | 20/20 | 20/20 |
| Oral dosing | 5 | 4/10 | 4/10 |
| | 10 | 0/15 | 1/15 |
| | 20 | 0/10 | 0/10 |
| Subcutaneous | 5 | 1/5 | 1/5 |
| dosing | 10 | 0/5 | 0/5 |

Crystals containing hygromycin (68%), epihygromycin (24%) and moisture (8%) were used.

TABLE 4

| Test group | Dosage (mg/kg/ day × 2) | Number of mice with caecal lesion/number of mice tested | Number of mice from which the organisms were recovered/number of mice tested |
|---|---|---|---|
| Infected, untreated control | — | 5/5 | 5/5 |
| Hygromycin | 5 | 1/5 | 2/5 |
| (oral dosing) | 10 | 0/5 | 2/5 |
| | 20 | 0/5 | 0/5 |
| Epihygromycin | 5 | 0/5 | 4/5 |
| (oral dosing) | 10 | 0/5 | 1/5 |
| | 20 | 0/5 | 0/5 |
| Mixture (oral dosing) | 10 | 0/5 | 0/5 |

Hygromycin, epihygromycin and a mixture thereof (the same as shown in Table 3) were used.

(iii) A study on the antidysenteric effects of hygromycin and epihygromycin in experimental swine dysentery was conducted. Fifteen piglets of Landrace strain, aged 7 to 9 weeks (at the time of infection with *Treponema hyodysenteriae*), were used. A liquid culture of *Treponema hyodysenteriae* HA17-f which was isolated from the mucohemorrhagic diarrheal feces of pigs affected by swine dysentery was added to an equal volume of physiological saline with 5% mucin, and 100 ml/animal of the mixture was inoculated into the stomach by a gastric catheter ($10^7$ CFU/animal).

Infected pigs were divided into 5 groups (A to E) of 3 individuals, and Group A was used as the infected, untreated control group. Pigs in Group B were fed for 7 days with a ration prepared by adding a mixture of hygromycin and epihygromycin to a domestically formulated starter feed without antibiotics (field formulated milk replacer B) for young pigs at a level of 50 ppm. To pigs in Group C, a solution of the same drug mixture in sterile water was injected into the gluteal muscle at a dose of 10 mg/kg body weight once a day for 3 consecutive days. For Group D and Group E, carbadox (Pfizer Taito) and tiamulin (Nippon Zenyaku) were added to the starter feed and the resulting medicated rations were given. In all groups, the courses of fecal consistency and fecal *Treponema hyodysenteriae* counts were examined every day. All of the animals were killed and submitted to autopsy within 10 days after initiation of treatment and the severity of large intestinal lesions, and the presence of *Treponema hyodysenteriae* in the large intestinal contents and mucosa were investigated. The results are summarized in Table 5. In regard to the groups treated with a mixture of hygromycin and epihygromycin, in both the dietary administration group and the intramuscular administration group, the fecal *Treponema hyodysenteriae* became negative by day 2 after initiation of treatment and continued to be negative until the end of the study (autopsy). The mucohemorrhagic diarrheal stools found at initiation of treatment recovered to normal by day 2 in early cases and by day 5 in delayed cases. At autopsy, a small number of *Treponema hyodysenteriae* was detected in the large intestinal mucosa from one animal in the intramuscular administration group, but, inclusive of this case, no characteristic dysenteric lesions in the large intestine were found at all. In contrast, in the carbadox-treated group, one of 3 animals died of swine dysentery and the remaining two animals continued to show diarrhea or mucohemorrhagic diarrheal stools until the end of the trial. In the tiamulin-treated group, stool property became normal by day 5 after medication in 2 of 3 animals but the remaining one pig continued to excrete diarrheal or mucohemorrhagic diarrheal feces until the end of the trial. In these control drug-treated groups, all pigs treated with control drugs; carbadox and tiamulin, excreted a large number of *Treponema hyodystenteriae* into feces up until the end of the trial and had serious large intestinal lesions and a large number of *Treponema hyodysenteriae* in the mucosa.

TABLE 5

| Test group | Pig No. (sex) | Courses of stool property and T. hyo. count — Days after start of treatment: 0 (Administration started) | 1 | 2 | 3 | 4 | 5 | 6 | 7 | 8 | 9 | 10 | At autopsy — T. hyo. count: Rectal contents | Large intestinal mucosa | Dysenteric lesions of large intestine |
|---|---|---|---|---|---|---|---|---|---|---|---|---|---|---|---|
| A | 1 (male) | (5.5) | (8.7) | (7.9) | (8.2) | (8.0) | (8.1) | (8.2) | (6.9) | (5.7) | (6.9) | | (7.0) | (7.9) | +++ |
| | 2 (female) | (7.8) | (7.8) | (7.9) | (7.8) | (7.7) | (7.4) | (6.0) | (6.5) | (6.1) | (6.6) | | (7.4) | (8.0) | +++ |
| | 3 (male) | (5.5) | (7.6) | (8.0) | (8.5) | (7.9) | (7.2) | (7.2) | (5.8) | (6.0) | (5.9) | | (7.0) | (8.2) | +++ |
| B | 4 (male) | (7.9) | (4.2) | (–) | (–) | (–) | (–) | (–) | (–) | (–) | (–) | | (–) | (–) | – |
| | 5 (male) | (7.9) | (3.7) | (–) | (–) | (–) | (–) | (–) | (–) | (–) | (–) | | (–) | (–) | – |
| | 6 (male) | (7.0) | (5.5) | (–) | (–) | (–) | (–) | (–) | (–) | (–) | (–) | | (–) | (–) | – |
| C | 7 (male) | ↓ (8.1) | ↓ (–) | ↓ (–) | (–) | (–) | (–) | (–) | (–) | (–) | (–) | | (–) | (–) | – |
| | 8 (male) | ↓ (6.9) | ↓ (3.8) | ↓ (–) | (–) | (–) | (–) | (–) | (–) | (–) | (–) | | (–) | (5.5) | – |
| | 9 (male) | ↓ (5.9) | ↓ (2.9) | ↓ (–) | (–) | (–) | (–) | (–) | (–) | (–) | (–) | | (–) | (–) | – |
| D | 10 (female) | (6) | (7) | (6) | (5) | (6) | (6) | (7)*1 | | | | | – | (7) | +++ |
| | 11 (male) | (7) | (4) | (5) | (5) | (5) | (5) | (7) | (6) | (5) | (5) | | (6) | (6) | ++ |
| | 12 (male) | (7) | (4) | (3) | (6) | (4) | (6) | (6) | (5) | (4) | (3) | | (–) | (6) | ++ |
| E | 13 (male) | (3) | (3) | (4) | (4) | (6) | (5) | (6) | (5) | (3) | (3) | | (–) | (4) | + |
| | 14 (female) | (5) | (5) | (7) | (5) | (6) | (6) | (5) | (5) | (3) | (3) | | (3) | (7) | + |
| | 15 (male) | (5) | (7) | (7) | (6) | (7) | (6) | (7) | (++++) | (++++) | (++++) | | (8) | (7) | +++ |

A: Infected, untreated group
B: Test drug treated group [A mixture of hygromycin (68%), epihygromycin (24%) and moisture (8%) was given in feed at the level of 50 ppm for 7 days]
C: Test drug treated group [A mixture of hygromycin (68%), epihygromycin (24%) and moisture (8%) was intramuscularly administered once a day for 3 days in a dose of 10 mg/kg body weight]
D: Control drug treated group [Carbadox was given in feed at the level of 50 ppm for 7 days]
E: Control drug treated group [Tiamulin was given in feed at the level of 50 ppm for 7 days]
: Normal stool
: Soft stool
: Diarrheal stool. This stool property was further classified into the four grades of (+) tp (++++) according to the degree of contamination with blood and/or mucous (mucous membrane).
T. hyo.: The figure in parentheses denotes the count of *Treponema hyodysenteriae* (log CFU/g); –(minus) means "less than detection limit ($10^2$ CFU/g)".
↓: Day of intramuscular injection
Autopsy: Autopsy was carried out on postmedication day 10 (in the case of No. 10 day 6), and the dysenteric lesions of the large intestine at autopsy were classified into the four grades of (–) to (+++).
*1 Death From these results, it was proved that hygromycin and epihygromycin had more potent activity against *Treponema hyodysenteriae* than carbadox and tiamulin which are known antidysenteric agents for pigs.

(iv) The acute toxicity of hygromycin and epihygromycin was studied in mice. The results are summarized in Table 6.

TABLE 6

| Route of administration | $LD_{50}$ (mg/kg) |
|---|---|
| Intraperitoneal | >400 |
| Oral | >2000 |

In the study, a mixture containing hygromycin (68%), epihygromycin (24%) and moisture (8%) was used.

What is claimed is:

1. A method for treatment of swine dysentery, which comprises administering to swine, as an active ingredient, an anti-dysenteric effective amount of hygromycin, epihygromycin or a mixture thereof.

2. A method according to claim 1, wherein the active ingredient is a mixture of hygromycin and epihygromycin.

3. A method according to claim 1, wherein the active ingredient is a mixture of hygromycin and epihygromycin in a ratio of 1:0.3-1 (w/w).

4. A method according to claim 1, wherein the active ingredient is a mixture of hygromycin and epihygromycin in a ratio of 1:0.3-0.5 (w/w).

* * * * *